US012626813B2

(12) United States Patent
    Stolikj et al.

(10) Patent No.: US 12,626,813 B2
(45) Date of Patent: May 12, 2026

(54) SCHEDULING DIAGNOSTIC TESTS FOR ON-SITE REPAIR OF MEDICAL IMAGING DEVICES

(71) Applicant: KONINKLIJKE PHILIPS N.V., Eindhoven (NL)

(72) Inventors: Milosh Stolikj, Eindhoven (NL); Mauro Barbieri, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 501 days.

(21) Appl. No.: 17/518,632

(22) Filed: Nov. 4, 2021

(65) Prior Publication Data

US 2022/0157444 A1     May 19, 2022

Related U.S. Application Data

(60) Provisional application No. 63/113,203, filed on Nov. 13, 2020.

(51) Int. Cl.
    G16H 40/40        (2018.01)
    G16H 40/20        (2018.01)
(52) U.S. Cl.
    CPC ............. G16H 40/40 (2018.01); G16H 40/20 (2018.01)
(58) Field of Classification Search
    CPC .................................................... G16H 40/40
    See application file for complete search history.

(56) References Cited

U.S. PATENT DOCUMENTS

| | | | |
|---|---|---|---|
| 6,353,445 B1 | 3/2002 | Babula | |
| 2009/0089092 A1* | 4/2009 | Johnson ................. | G16H 40/60 |
| | | | 705/2 |
| 2015/0241542 A1* | 8/2015 | Choe ...................... | G01R 33/58 |
| | | | 324/318 |
| 2019/0272475 A1* | 9/2019 | Hegendoerfer ..... | G06F 11/2294 |
| 2020/0398054 A1* | 12/2020 | Errico ................. | G06K 7/1413 |

FOREIGN PATENT DOCUMENTS

| | | |
|---|---|---|
| EP | 0663623 | 7/1995 |
| WO | 2007014027 | 2/2007 |
| WO | 2017087566 | 5/2017 |
| WO | 2020046372 | 3/2020 |

* cited by examiner

*Primary Examiner* — Reginald R Reyes

(57) ABSTRACT

A method (100) of scheduling diagnostic tests for a medical device (2) between or during medical imaging examinations includes: receiving a schedule (30) of medical imaging examinations (32), the schedule providing start times of the medical imaging examinations, and time intervals between medical imaging examinations; fitting diagnostic tests (34) of a set (S) of diagnostic tests into the time intervals between or during the medical imaging examinations in the schedule to generate an updated schedule (36) of the medical imaging examinations and the set of diagnostic tests; and displaying the schedule of the medical imaging examinations and the set of diagnostic tests on a display device (24, 33) in operative communication with the electronic processor (16).

19 Claims, 3 Drawing Sheets

Receive schedule of medical exams — 102

Fit diagnostic tests into time intervals between or during imaging exams to generate an updated schedule — 104

Display updated schedule — 106

100

SCHEDULING DIAGNOSTIC TESTS FOR ON-SITE REPAIR OF MEDICAL IMAGING DEVICES

CROSS REFERENCE TO RELATED APPLICATIONS

This application is claims the benefit of U.S. Provisional Patent Application No. 63/113,203 filed Nov. 13, 2020. This application is hereby incorporated by reference herein.

FIELD

The following relates generally to medical device maintenance arts, medical imaging device examination and maintenance arts, maintenance services, diagnostic scheduling arts, and related arts.

BACKGROUND

Medical devices occasionally exhibit a malfunction, which requires maintenance. Depending on the malfunction, the problem can sometimes be handled remotely by a remote service engineer (RSE). The RSE can perform a remote diagnostic test by analyzing the log data generated from the malfunctioning medical device, or by remotely executing diagnostic tests. In certain situations, the RSE can successfully resolve the issue completely remotely.

However, for certain malfunctions, remote resolution is not possible. In such situations, in addition to the remote diagnostic test, a field service engineer (FSE) has to visit the physical location of the medical device and perform on-site maintenance. During these visits, the FSE may need to perform additional diagnostic tests to discover the root cause of the issue, and/or replace parts of the imaging device. Sometimes, due to lack of time, lack of replacement part(s), or incomplete diagnostic, the FSE has to perform multiple visits before the problem is resolved.

Certain diagnostic tests are extensive and hence require a lot of time to complete. Running these tests during on-site maintenance has a negative impact on the users of the machine, since the downtime of the machine increases. It also extends the time the FSE has to spend on site, which has a negative financial impact for the maintenance operator.

The following discloses certain improvements to overcome these problems and others.

SUMMARY

In one aspect, a non-transitory computer readable medium stores instructions executable by at least one electronic processor to perform a method of scheduling diagnostic tests for a medical device between or during medical imaging examinations. The method includes: receiving a schedule of medical imaging examinations, the schedule providing start times of the medical imaging examinations, and time intervals between medical imaging examinations; fitting diagnostic tests of a set of diagnostic tests into the time intervals between or during the medical imaging examinations in the schedule to generate an updated schedule of the medical imaging examinations and the set of diagnostic tests; and displaying the schedule of the medical imaging examinations and the set of diagnostic tests on a display device in operative communication with the electronic processor.

In another aspect, a non-transitory computer readable medium stores instructions executable by at least one electronic processor to perform a method of scheduling diagnostic tests for a medical device between or during medical imaging examinations. The method includes: receiving a schedule of medical imaging examinations, the schedule providing start times of the medical imaging examinations, and time intervals between medical imaging examinations; fitting diagnostic tests of a set of diagnostic tests into the time intervals between or during the medical imaging examinations in the schedule to generate an updated schedule of the medical imaging examinations and the set of diagnostic tests including performing a bin packing operation on the schedule of the medical imaging examinations to generate the schedule of the medical imaging examinations and the set of diagnostic tests, wherein bins of the bin packing operation correspond to the time intervals between or during medical examinations into which one or more diagnostic tests are inserted; and displaying the schedule of the medical imaging examinations and the set of diagnostic tests on a display device in operative communication with the electronic processor.

In another aspect, a method of scheduling diagnostic tests for a medical device between medical imaging examinations includes: receiving a schedule of medical imaging examinations, the schedule providing start times of the medical imaging examinations, and time intervals between medical imaging examinations; fitting diagnostic tests of a set of diagnostic tests into the time intervals between or during the medical imaging examinations in the schedule to generate an updated schedule of the medical imaging examinations and the set of diagnostic tests, wherein the fitting includes a bin packing operation; and displaying the schedule of the medical imaging examinations and the set of diagnostic tests on a display device in operative communication with the electronic processor.

One aspect resides in reducing down-time of a medical device during an on-site maintenance visit.

Another advantage resides in adjusting a schedule of medical examinations to include diagnostic tests of a medical device.

Another advantage resides in improving efficiency of an on-site visit to service a medical device.

Another advantage resides in reducing a negative financial impact for a medical facility due to downtime of a medical device.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
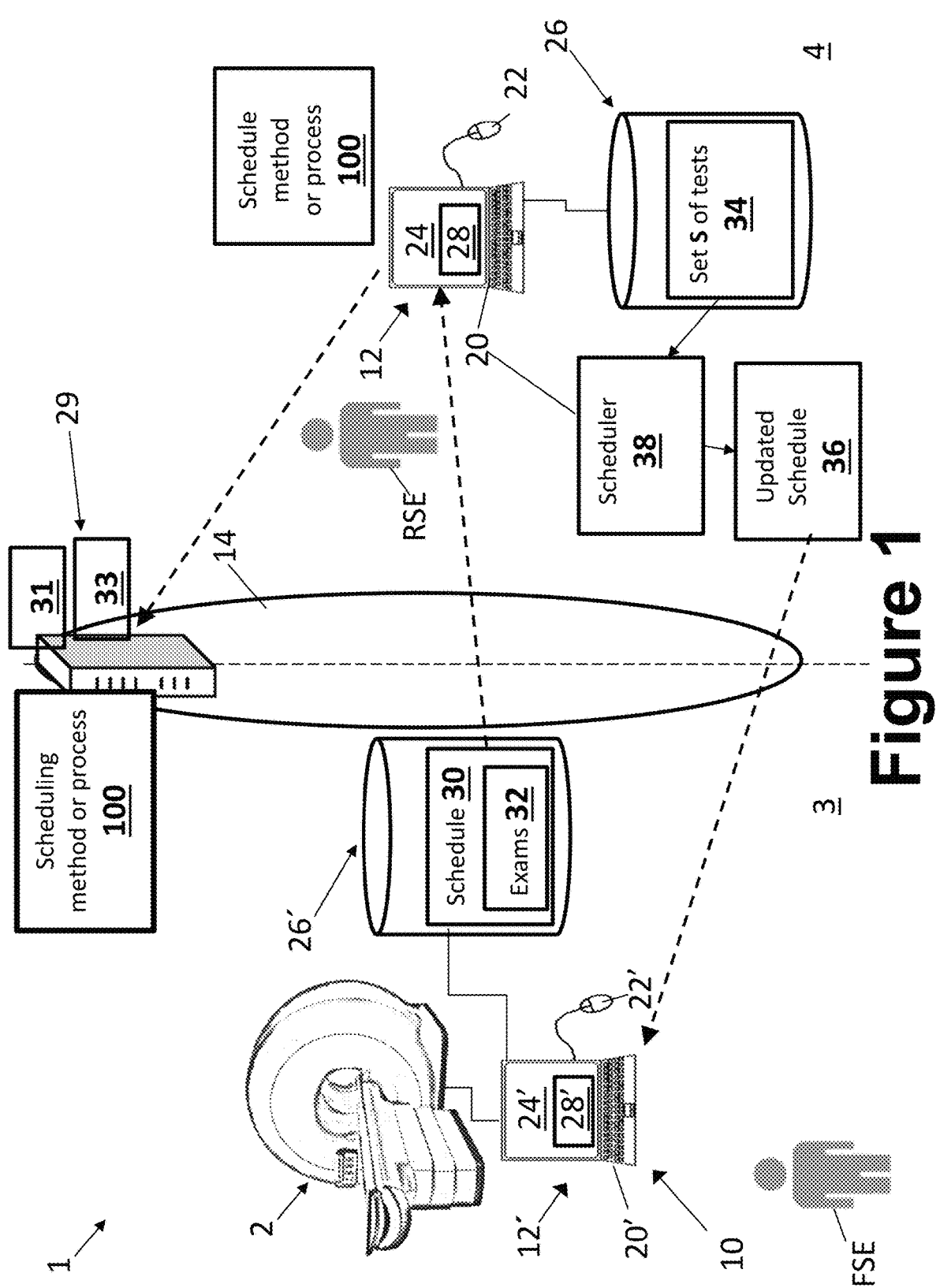
FIG. 1 diagrammatically illustrates an illustrative system scheduling diagnostic tests between medical imaging sessions in accordance with the present disclosure.

On-site maintenance can be performed by field service engineers (FSEs) and remote maintenance performed by remote service engineers (RSEs). Usually, a RSE is initially consulted when a customer (e.g. hospital) calls for service. The RSE has a workstation that provides fault-finding diagnostics, a schedule of FSE availability, and remote imaging device control software. The RSE may determine that one or more diagnostic tests are needed, with the workflow (including whether an FSE must be sent out to the customer) being determined based on the results of the diagnostic tests. To perform the diagnostic tests, three approaches may be taken.

First, the RSE may directly perform a diagnostic test via the remote imaging device control software. This may be feasible if the diagnostic test is purely software-based (e.g. running software diagnostics that do not require controlling the imaging hardware), and may also be feasible if the diagnostic test can be performed with an empty imaging region.

Second, the RSE may request that customer personnel (e.g. an imaging technician) perform a remote diagnostic test. This may be a good approach if the diagnostic test requires imaging a phantom which must be physically loaded into the imaging region, or requires some other hardware modification (e.g. loading a specific X-ray filter), and if the diagnostic test is one the imaging technician is qualified to perform.

Third, the RSE may schedule an FSE to visit the customer to perform the diagnostic test. This may be a good approach if the test requires manipulation of the imaging device hardware that cannot be done remotely, and if customer personnel are uncomfortable with performing the diagnostic test. However, sending an FSE out to perform a diagnostic test can be inefficient, since the next action in the workflow is usually not known until the result of the test becomes available. So, for example, if the diagnostic test indicates a solution that can be performed remotely then the FSE visit was arguably unnecessary. Or, if the diagnostic test indicates a solution that requires ordering a part, then the FSE will need to come back to install the part in a subsequent visit to the customer.

To improve efficiency, the following proposes to automatically, or semi-automatically, schedule diagnostic tests between or during imaging examinations. To this end, the RSE workstation is modified to include (i) an imaging examinations schedule loader and (ii) a schedule optimizer.

The hospital schedule loader can take various forms depending on how well the RSE workstation is integrated with a hospital information system (HIS). In a fully automated embodiment, the RSE workstation sends an authenticated query to the HIS which responds by sending an electronic version of the imaging examinations schedule. In a more semi-automated approach, hospital personnel send the imaging examinations schedule to the RSE in a portable format such as an Excel worksheet, and the loader comprises a script that reads the Excel worksheet (or, in an even less automated approach, the loader simply provides a user interface via which the RSE manually types the schedule in).

The schedule optimizer attempts to fit the diagnostic tests into intervals between or during imaging examinations. The examinations are assumed to be spaced apart by time gaps of some minimum duration. Additionally, the (scheduled) start times and durations of all imaging examinations are assumed to be known, as well as the durations of the diagnostic tests, and required resource requirements (e.g., CPU, memory, and so forth). These are reasonable assumptions since the examinations schedule usually defines these values for the examinations, and the diagnostic tests have at least approximately a priori known durations. Finally, a time limit on the diagnostic tests is imposed, which usually corresponds to the time the FSE is expected to visit (the rationale being that all diagnostic tests are preferably completed before the FSE visit).

In the schedule optimization, there are three possible variables to adjust: the start times of the diagnostic tests, the start times of the imaging examinations, and the time limit (which may be extended if it is impossible to schedule all diagnostic tests within the time limit). However, it is preferable to avoid adjusting start times of the imaging examinations since this imposes a burden on the customer. Similarly, it is preferable to avoid extending the time limit as this will delay resolution of the customer's issue, which can adversely impact customer satisfaction and may also incur a financial cost (e.g., if the service contract imposes a monetary penalty for delayed servicing).

The following provides a detailed disclosure of how the foregoing problem can be formulated as a standard bin packing problem, where the "bins" are the slots between examinations into which diagnostic tests are to be inserted, or time intervals within medical examinations during which diagnostic tests can be run in parallel. There are standard solutions for the standard bin packing problem, and examples thereof are included herein.

Furthermore, the following proposes a two- or three-step process. In the first step, solution of the bin packing problem is attempted with only the start times of the diagnostic tests as adjustable variables. If this is impossible (e.g., if a diagnostic test length is longer than the longest available interval between imaging examinations), then in a second step, the imaging examination start times are also treated as adjustable variables. In an optional third step, if the first and second steps both fail then the time limit can also be extended.

If/when a suitable optimized schedule is determined, it may be used in various ways. In one approach, it is presented to the RSE on the workstation, and the RSE consults via telephone with the customer to propose the schedule. Alternatively, if the HIS/RSE workstation integration is sufficient then the optimized schedule may be used to directly (i.e. electronically) modify the examinations schedule at the HIS. Such automatic modification may be limited to certain situations, such as when diagnostic tests are only being scheduled between imaging examinations but without modifying the start times of any examinations.

In some embodiments disclosed herein, the schedule of FSE availability may be consulted to set the time limit. Optionally, the time limit may be treated as an additional adjustable variable which is weighted by a cost factor reflecting a late-service contract penalty.

In other embodiments disclosed herein, the schedule optimizer may be run dynamically to adjust the schedule of diagnostic tests in real time to reflect changing conditions such as FSE availability, changes in the hospital's examination schedule, or so forth.

In some embodiments disclosed herein, different types of diagnostic tests may be treated differently for scheduling purposes. Notably, a diagnostic test that does not require use of only the hardware of the imaging system (i.e. a non-hardware-only diagnostic test) may be scheduled in between medical imaging examinations with an imaging examination so long as there is sufficient CPU time and memory. For this variant embodiment, the bin packing problem formulation can be modified to allow for scheduling of imaging examinations and non-hardware-only diagnostic tests.

With reference to FIG. 1, an apparatus 1 for scheduling diagnostic tests between or during medical imaging sessions is shown. As shown in FIG. 1, a FSE performs service on a medical imaging device (also referred to as an image acqui-sition device, imaging device, and so forth) 2, is located in a medical imaging device bay 3. A RSE who helps schedule the diagnostic tests is disposed in a remote service location or center 4. The remote location 4 can be a remote service center, a radiologist's office, a radiology department, and so forth. The remote location 4 may be in the same building as the medical imaging device bay 3, but more typically the remote service center 4 and the medical imaging device bay 3 are in different buildings, and indeed may be located in different cities, different countries, and/or different conti-nents. In general, the remote location 4 is remote from the imaging device bay 3 in the sense that the RSE cannot directly visually observe the imaging device 2 in the imag-ing device bay 3.

The image acquisition device 2 can be a Magnetic Reso-nance (MR) image acquisition device, a Computed Tomog-raphy (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acqui-sition devices, which may be of the same and/or different imaging modalities. For example, if a hospital performs many CT imaging examinations and relatively fewer MRI examinations and still fewer PET examinations, then the hospital's imaging laboratory (sometimes called the "radi-ology lab" or some other similar nomenclature) may have three CT scanners, two MRI scanners, and only a single PET scanner. This is merely an example. Moreover, the remote service center 4 may provide service to multiple hospitals. The medical imaging device 2 includes an imaging device controller 10. The RSE is stationed at a remote workstation 12 (or, more generally, an electronic controller 12).

As used herein, the term "medical imaging device bay" (and variants thereof) refer to a room containing the medical imaging device 2 and also any adjacent control room con-taining the medical imaging device controller 10 for con-trolling the medical imaging device. For example, in refer-ence to an MRI device, the medical imaging device bay 3 can include the radiofrequency (RF) shielded room contain-ing the MRI device 2, as well as an adjacent control room housing the medical imaging device controller 10, as under-stood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote operator RSE and FSE ends for electronic data communications.

FIG. 1 also shows, in the remote service center 4 includ-ing the remote workstation 12, such as an electronic pro-cessing device, a workstation computer, or more generally a computer, which is operatively connected to the imaging device controller 10. Additionally or alternatively, the remote workstation 12 can be embodied as a server computer or a plurality of server computers, e.g. interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, e.g. one display presenting schedule of medical examinations and the other presenting a set diag-nostic tests to be performed for the imaging device 2. Alternatively, the schedule a set of tests may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic pro-cessor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10, which includes a local workstation 12' disposed in the medical imaging device bay 3, similar to those of the remote workstation 12 disposed in the remote service center 4 have a common reference number followed by a "prime" symbol, and the description of the components of the medical imaging device controller 10 will not be repeated. In particular, the medical imaging device controller 10 is configured to display a GUI 28' on a display device or controller display 24' that presents infor-mation pertaining to the control of the medical imaging device 2, such as configuration displays for adjusting con-figuration settings, an alert perceptible at the remote location when the status information on the medical imaging exami-nation satisfies an alert criterion of the imaging device 2, imaging acquisition monitoring information, presentation of acquired medical images, and so forth. The communication link 14 can allow for screen sharing between the display device 24 in the remote service center 4 and the display device 24' in the medical imaging device bay 3. The GUI 28' includes one or more dialog screens, including, for example, an examination/scan selection dialog screen, a scan settings dialog screen, an acquisition monitoring dialog screen, among others.

Furthermore, as disclosed herein the remote workstation 12 performs a method or process 100 of scheduling diag-nostic tests for a medical device 2 between or during medical imaging examinations. the non-transitory computer readable medium 26 of the remote workstation 12 stores instructions executable by the at least one electronic processor 20 to perform the method 100. The FIG. 1 also shows the remote workstation 12 and the medical imaging device controller 10 in communication with a network-based server computer 29. The server computer 29 can comprise an associated hospital scheduling system that is configured to perform the method 100. The hospital scheduling system 29 can also include a display device 33.

The non-transitory computer readable medium 26' of the medical imaging device controller 10 stores a schedule 30 of medical examinations 32 (i.e., imaging examinations) for a time period, e.g., a day. The schedule 30 provides start times of the medical examinations 32, along with time intervals between the examinations. This information can be provided by the schedule 30 in various ways, such as by providing start times and end times of the medical examinations 32, or by providing start times and durations of the medical examinations 32.

In addition, the non-transitory computer readable medium 26 of the remote workstation 12 stores a set S of diagnostic tests 34 to be performed on the medical imaging device 2. As described in more detail below, the method 100 includes fitting some or all of the diagnostic tests 34 of the set S of diagnostic tests into the time intervals between or during the medical examinations 32 to generate an updated schedule 36. To do so, the remote workstation 12 (or the network based server computer 29) is programmed to implement a scheduling module 38 in order to fit the diagnostic tests 34 into the time intervals between the medical examinations 32 to generate the updated schedule 36.

Figure 2:
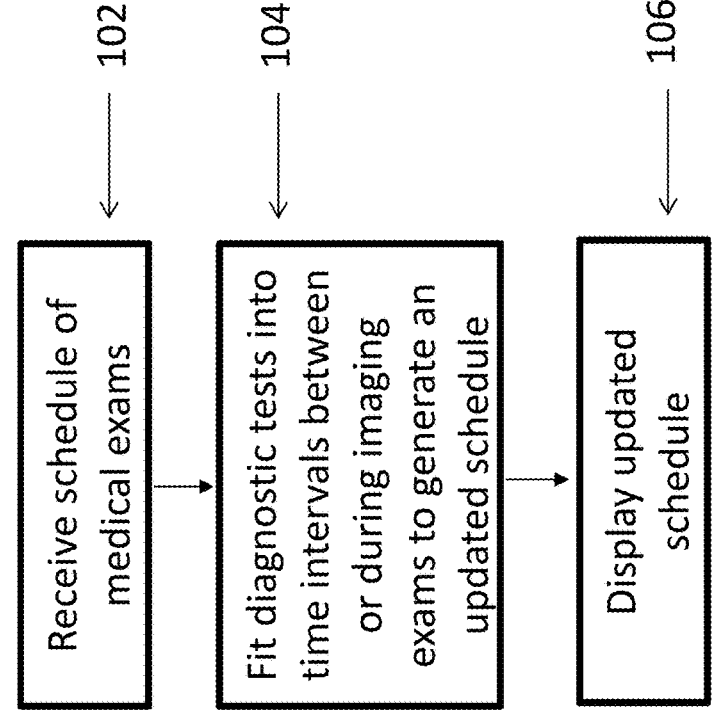
FIGS. 2 and 3 show exemplary flow chart operations of the system of FIG. 1.

With reference to FIG. 2, and with continuing reference to FIG. 1, an illustrative embodiment of the method 100 is diagrammatically shown as a flowchart. At an operation 102, the schedule 30 is received. In some embodiments, the schedule 30 is transmitted from the medical imaging device controller 10 to the remote workstation 12. In other embodiments, the remote workstation 12 queries the hospital scheduling system 29 via the electronic network 14 to request the schedule, and receives the schedule responsive to the query. In some examples, the schedule 30 can be received in a portable format, such as a spreadsheet, or as an email attachment. In other examples, inputs comprising the schedule 32 to the medical imaging device controller 10 (e.g., via the FSE using the at least one user input device 22') can be transmitted to the remote workstation 12. In addition, the RSE can input the schedule 32 as inputs using the at least one user input device 22.

At an operation 104, the diagnostic tests 34 of the set S of diagnostic tests into the time intervals between or during the medical imaging examinations 32 in the schedule 30 to generate the updated schedule 36. The fitting operation 104 can be performed the scheduler module 38. The fitting operation 104 can only be done if the set of diagnostics tests 34 is known apriori. The fitting operation 104 could be re-run if a new diagnostics test 34 is added, or one is removed, but that would be a second iteration). The fitting operation 104 can be performed in a variety of matters.

In some embodiments, the fitting operation 104 includes imposing a time limit on completion of the set (S) of diagnostic tests 34. For example, all diagnostic tests 34 of the set S of diagnostic tests are fitted into the time intervals between or during the medical imaging examinations 32 that precede or end with the imposed time limit.

In some examples, the fitting operation 104 includes multiple iterations. For example, in a first fitting operation, the diagnostic tests 34 are fit into the time intervals between the medical imaging examinations 32 that precede or end with the imposed time limit. If the first fitting operation fails, then the imposed time limit is extended to define an extended time limit and, in a second fitting operation, the diagnostic tests 34 are fit into the time intervals between or during the medical imaging examinations 32 that precede or end with the extended time limit.

In other embodiments, in another example of multiple fitting operations, the diagnostic tests 34 are fit into the time intervals between or during the medical imaging examinations 32 by adjusting only assignments of the diagnostic tests to the time intervals between or during the medical imaging examinations. If the first fitting operation fails, then in a second fitting operation, the diagnostic tests 34 are fit into the time intervals between or during the medical imaging examinations 32 by adjusting both the start times of the medical imaging examinations and the assignments of the diagnostic tests of the set of diagnostic tests to the time intervals between or during the medical imaging examinations.

In this embodiment, the first fitting operation and the second fitting operation are each performed with a time limit on completion of the set S of diagnostic tests 34. All diagnostic tests 34 are fitted into the time intervals between or during the medical imaging examinations 32 that precede or end with the imposed time limit. If the second fitting operation fails, then a third fitting operation is performed. In the third fitting operation, the diagnostic tests 34 are fit into the time intervals between or during the medical imaging examinations by adjusting at least the assignments of the diagnostic tests of the set of diagnostic tests to the time intervals between or during the medical imaging examinations 32 with a longer time limit on the completion of the set of diagnostic tests than the time limit used in the first and second fitting operations. The third fitting operation with the extended time limit could be performed with or without adjusting the start times. In other examples, the first and second fitting operations can be repeated with the extended time limit, to try to avoid needing to adjust the start times (since that might then be possible with the extended time limit).

In further embodiments, the fitting operation 104 includes performing a bin packing operation to generate the updated schedule 36. To do so, bins of the bin packing operation correspond to the time intervals between or during medical examinations 30 into which one or more diagnostic tests 34 are inserted. The bins can include adjustable variables. In some examples, the adjustable variables of the bin packing operation include only allocations of the diagnostic tests 34 to the bins corresponding to the time intervals. That is, in the tri-iteration embodiment of the fitting operation 104, the first iteration tries to fit the diagnostics tests 34 in the schedule 30 by only adjusting the allocations of diagnostic tests to time intervals/bins. The adjustable variables comprise only those allocations. The start times of the medical examinations 30 are not adjustable variables; rather, those start times are fixed values, or "variables". In other examples, the adjustable variables can include allocations of the diagnostic tests 34 to the bins corresponding to the time intervals, along with start times of the medical imaging examinations 30. Thus, in this example the start times are adjustable variables. In further examples, the adjustable variables can include a time limit on completion of the set S of diagnostic tests 34. In this example, all diagnostic tests 34 are fitted by the bin packing operation into the time intervals between or during the medical imaging examinations 32 that precede or end with the time limit on completion of the set of diagnostic tests.

In yet other examples, the fitting operation 104 can include adjusting a time limit for completion of the set (S) of diagnostic tests 34 including weighting the adjustment of the time limit with a cost factor reflecting a late-service contract penalty. That is, a penalty can be imposed if the diagnostic test 34 medical examinations 30 are not scheduled in such a way that reduces downtime of the image acquisition device 2. In other examples, a scope of the diagnostics tests 34 (e.g., what each test entails) can be determined to fit the diagnostic tests into the time intervals between medical examinations 32 (i.e., longer diagnostic tests 34 are fitted into longer time intervals between medical examinations).

In other examples, the fitting operation 104 includes retrieving a maintenance personnel availability schedule 31 (e.g., from the hospital scheduling system 29). A time limit can be set for completion of the diagnostic sets 34 based on the maintenance personnel availability schedule 31.

In more examples, the fitting operation 104 is repeated iteratively to dynamically update the updated schedule 36 of the medical imaging examinations 32 and the set S of diagnostic tests 34 to account for changes over time in the set of diagnostic tests and/or changes in the schedule 30 of medical imaging examinations.

At an operation 106, the updated schedule 36 of the medical imaging examinations 32 and the set S of diagnostic tests 34 is displayed on a display device in operative communication with the electronic processor 20. In some examples, the updated schedule 36 can be displayed on the display device 24' of the medical imaging device controller 10. In other examples, the updated schedule 36 is sent to the hospital scheduling system 29 via the electronic network 14. The updated schedule 36 can be displayed on the display device 33 of the hospital scheduling system 29. In some examples, the updated schedule 36 can be displayed at both the medical imaging device controller 10 and the hospital scheduling system 29.

Figure 3:
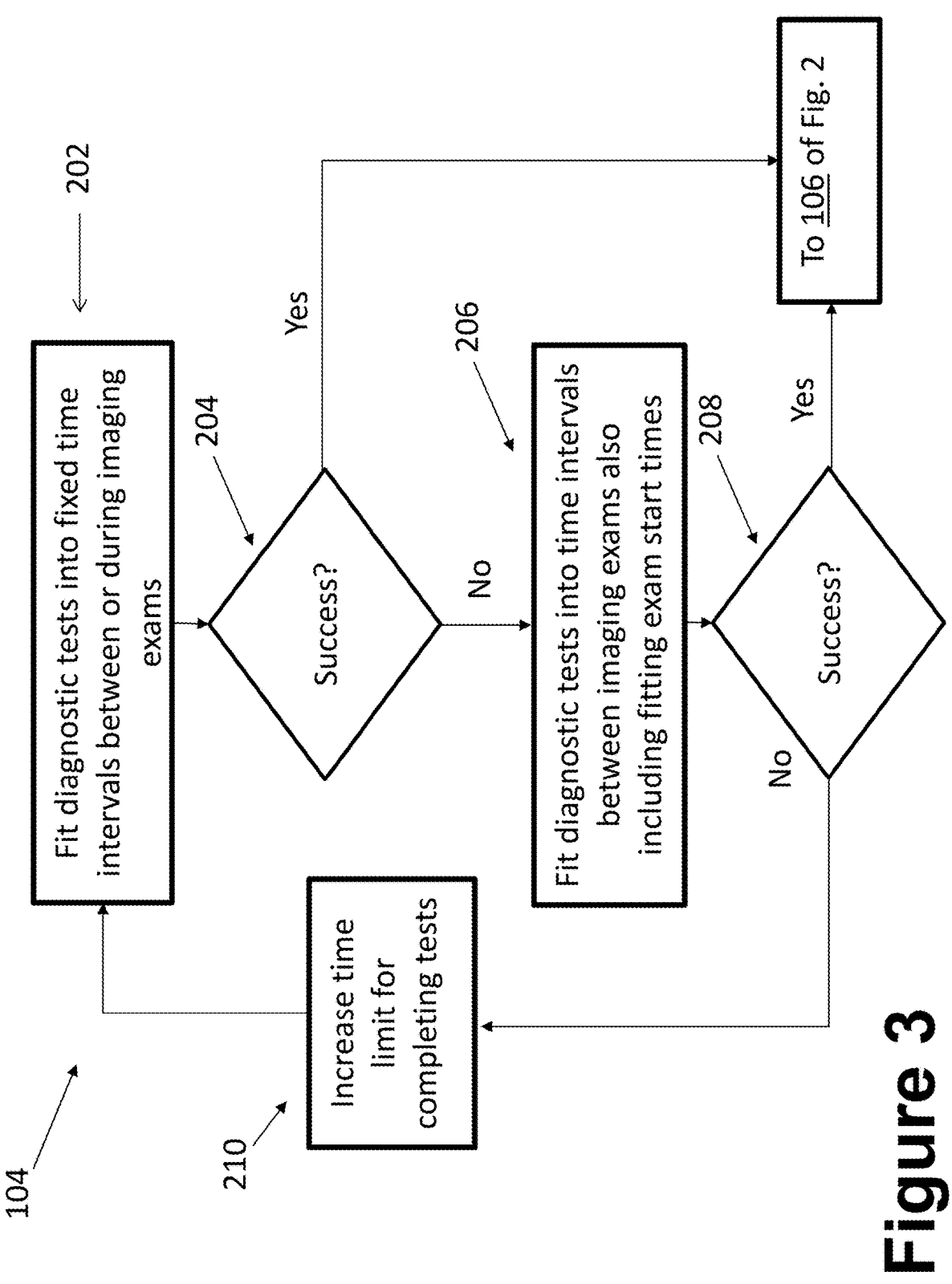

FIG. 3 diagrammatically shows an illustrative embodiment of the operation 104 as a flowchart as described above. At an operation 202, in the first fitting operation, the diagnostic tests 34 of the set S of diagnostic tests into the time intervals between or during the medical imaging examinations 32 that precede or end with the imposed time limit. If the first fitting operation 202 is determined to be successful (illustrated at the decision block 204), then the method 100 proceeds to the displaying option 106 of FIG. 2. If the first fitting operation 202 is determined to be unsuccessful, then the method 100 moves to an operation 206.

At the operation 206, in the second fitting operation, the diagnostic tests 34 of the set S of diagnostic tests are fit into the time intervals between or during the medical imaging examinations 32 by adjusting both the start times of the medical imaging examinations and the assignments of the diagnostic tests of the set of diagnostic tests to the time intervals between or during the medical imaging examinations. If the second fitting operation 206 is determined to be successful (illustrated at the decision block 208), then the method 100 proceeds to the displaying option 106 of FIG. 2. If the second fitting operation 206 is determined to be unsuccessful, then the method 100 moves to an operation 210.

At the operation 210, in the third fitting operation, the diagnostic tests 34 of the set S of diagnostic tests are fit into the time intervals between or during the medical imaging examinations 30 by adjusting at least the assignments of the diagnostic tests to the time intervals between or during the medical imaging examinations with a longer time limit on the completion of the set of diagnostic tests than the time limit used in the first and second fitting operations. The method 100 then proceeds back to the first fitting operation 202. The fitting operation 104 is then repeated until one of the fitting operations 202, 26, 210 are successful, and then the method 100 proceeds to the displaying operation 106.

EXAMPLE

The following describes implementation of the scheduler module 38. As described herein, the set S of diagnostic tests 34 is executed after the FSE arrives on site, that the diagnostic tests are remotely scheduled and uploaded by the scheduler module 38 (if needed) beforehand. Then the FSE visit can be planned after all diagnostic tests 34 are expected to be completed. Here, two alternatives are considered, depending on whether during scheduling of the diagnostic tests 34, the expected workload of the medical imaging device 2 is known for the coming period or not.

If the planned workload is known, then the diagnostic tests 34 are scheduled during slots between or during scheduled work of the medical device 2. If the planned workload is not known, then the available slots for completing the diagnostic tests 34 are defined manually, by e.g. pre-setting off-peak hours (night shifts), or by agreement with the operator of the medical device 2. In both cases, it can be calculated when all diagnostic tests 34 can be completed. Therefore, the FSE visit can be planned after that moment. In case the calculated time of the FSE visit is deemed to be too late, then the scheduler module 38 may offer to re-schedule certain medical examinations 32 (e.g. increase the time between exams), in order to reduce the total time required to complete all diagnostic tests 34.

Thus, the scheduler module 38 potentially reduces the time spent by the FSE on site during maintenance and reduces the overall downtime of the medical device 2.

To formally describe the problem, the notation is used as introduced in M. R. Garey and R. L. Grahams: Bounds For Multiprocessor Scheduling With Resource Constraints, SIAM Journal of Computing. Vol. 4, No. 2, June 1975. Let $R=\{R_1, R_2, \ldots R_n\}$ denote the set of resources that the device has. The total amount of each resource $R_i$ is 1.

Let $T=\{T_1, T_2, \ldots T_m\}$ be the set of tasks that should be executed on the medical device. Each task j can be either a diagnostic test, or a patient exam. This is defined by:

$$e(T_j) = \begin{cases} 0, & \text{task is a diagnostic test} \\ 1, & \text{task is a patient exam} \end{cases}$$

Each task j has an exact execution time of $t(T_j)$, and requires the use of $R_i(T_j)$ units of resource $R_i$ for the full duration of its execution, with $0 \leq R_i(T_j) \leq 1$, for every i. All tasks are assumed to be independent of each other, and can be executed in any order, though this framework can be extended to handle dependencies as well.

The medical device 2 starts execution at time 0. The final execution time, denoted by co, is defined as the time when all tasks have completed. Let $F:T \rightarrow 2^{[0, \infty)}$ be defined by $F(T_j)=[\sigma_j, \sigma_j+t(T_j))$, where $\sigma_i$ is the time when the execution of task $T_j$ started. The set of tasks executing at time t is then defines as f (t):

$$f:[0,\infty) \rightarrow 2^T,$$

$$f(t)=\{T_i \in T: t \in F(T_i)\}$$

Within this scenario, the following constrains must be satisfied. At any given point in time t, only the available resources can be used:

$$\sum_{T_j \in f(t)} R_i(T_j) \leq 1, \text{ for every } t \in [0,\omega), \text{ for every } i \in [1,n] \qquad 5$$

and at any given point in time t, at most one exam can be run:

$$\sum_{T_j \in f(t)} e(T_j) \leq 1, \text{ for every } t \in [0,\omega)$$

The goal is to find a mapping F that minimizes ω. This is a well-known problem in job scheduling and can be solved by many algorithms (e.g. first come first serve, shortest job first, best fit etc.).

In a first extension, some medical imaging examinations 30 are already planned, and the time when they scheduled for execution is known and fixed beforehand. The remaining medical imaging examinations 30 and diagnostic tests 34 need to be scheduled in the available times/resources. In this case, the mapping function F is partially known, and the same solution as before can be used to schedule the remaining tasks.

In a second extension, instead of directly minimizing the total execution time co, the cost for the maintenance operator is minimized. This cost can depend on external factors, such the repair moment (weekday/weekend), the travel plan of the medical imaging examinations 30, the contract between the hospital and the maintenance operator etc. In this case the cost is a function of the time when all diagnostic tests have been completed $\omega_d$, defined as:

$$\omega_d = \max\{\max(F(T_j)):T_j \in T / \backslash e(T_j)=0\}.$$

For example, if a medical imaging device 2 has malfunction, and the RSE concludes that an image quality assessment of completed scans has to be performed in order to decide on the replacement to be made. For the image quality assessment, two diagnostic tests 34 are deemed necessary. Each diagnostic test 34 verifies that a particular part is operating properly, and the two diagnostic tests verify the operation of two different parts. Each diagnostic test 34 takes exactly 30 minutes to complete. In the upcoming 14 hours, the medical device is scheduled to have patients at the start of every hour, and each patient exam takes exactly 45 minutes. The medical device 2 has one resource, and all diagnostic tests 34 and medical imaging examinations 30 use the resource in full while they are executing. This scenario can be modeled as:

$R=\{R_1\}$, i.e. one resource $T=\{T_1, T_2, \ldots T_{16}\}$, i.e. 16 tasks in total $$e(T_j) = \begin{cases} 0, & j \in \{15, 16\} \\ 1, & j \in \{1, 2, \ldots 14\} \end{cases},$$

i.e. tasks 1-14 are exams, 15-16 are diagnostic tests $$t(T_j) = \begin{cases} 30, & j \in \{15, 16\} \\ 45, & j \in \{1, 2, \ldots 14\} \end{cases},$$

i.e. the duration of the diagnostic tests is 30 minutes, while the duration of the exams is 45 minutes When the patient schedule is pre-determined, the mapping function F is partially defined by:

$$F(T_j)=[(j-1)\cdot 60,(j-1)\cdot 60+t(T_j)),j\in\{1,2,\ldots,14\}$$

Based on this schedule, the diagnostic tests 34 can be scheduled at the earliest after exam 14 finishes:

$$F(T_{15})=[825,855)$$

$$F(T_{16})=[855,885)$$

Therefore, the earliest time the FSE can be scheduled is after 14:45 (885 minutes after the start). If this is too late, an alternative schedule can be proposed, where medical imaging examinations 30 are tightly packed one after each other. In this schedule, each diagnostic test 34 is scheduled after 6 patients. Both tests have completed by 10:00, and the FSE visit can be scheduled after this time:

$$F(T_j)=[(j-1)\cdot t(T_j)),j\cdot t(T_j)),j\in\{1,2,\ldots,6\}$$

$$F(T_{15})=[270,300)$$

$$F(T_j)=[(j-7)\cdot t(T_j)+300,(j-6)\cdot t(T_j)+300),j\in \{7,8,\ldots,12\}$$

$$F(T_{16})=[570,600)$$

$$F(T_j)=[(j-13)\cdot t(T_j)+600,(j-12)\cdot t(T_j)+600),j\in\{13,14\}$$

Both schedules are shown in Table 1.

TABLE 1

| Task | Start time | End time |
|---|---|---|
| | Schedule 1 | |
| Patient 1 | 00:00 | 00:45 |
| Patient 2 | 01:00 | 01:45 |
| Patient 3 | 02:00 | 02:45 |
| Patient 4 | 03:00 | 03:45 |
| Patient 5 | 04:00 | 04:45 |
| Patient 6 | 05:00 | 05:45 |
| Patient 7 | 06:00 | 06:45 |
| Patient 8 | 07:00 | 07:45 |
| Patient 9 | 08:00 | 08:45 |
| Patient 10 | 09:00 | 09:45 |
| Patient 11 | 10:00 | 10:45 |
| Patient 12 | 11:00 | 11:45 |
| Patient 13 | 12:00 | 12:45 |
| Patient 14 | 13:00 | 13:45 |
| Test 1 | 13:45 | 14:15 |
| Test 2 | 14:15 | 14:45 |
| | Schedule 2 | |
| Patient 1 | 00:00 | 00:45 |
| Patient 2 | 00:45 | 01:30 |
| Patient 3 | 01:30 | 02:15 |
| Patient 4 | 02:15 | 03:00 |
| Patient 5 | 03:00 | 03:45 |
| Patient 6 | 03:45 | 04:30 |
| Test 1 | 04:30 | 05:00 |
| Patient 7 | 05:00 | 05:45 |
| Patient 8 | 05:45 | 06:30 |
| Patient 9 | 06:30 | 07:15 |
| Patient 10 | 07:15 | 08:00 |
| Patient 11 | 08:00 | 08:45 |
| Patient 12 | 08:45 | 09:30 |
| Test 2 | 09:30 | 10:00 |
| Patient 13 | 10:00 | 10:45 |
| Patient 14 | 10:45 | 11:30 |

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of scheduling and performing diagnostic tests for a medical imaging device between or during medical imaging examinations, the method comprising:

receiving a schedule of medical imaging examinations, the schedule providing start times of the medical imaging examinations, and time intervals between medical imaging examinations;

fitting diagnostic tests of a set of diagnostic tests into the time intervals between or during the medical imaging examinations in the schedule to generate an updated schedule of the medical imaging examinations and the set of diagnostic tests by performing a bin packing operation on the schedule of the medical imaging examinations to generate the updated schedule of the medical imaging examinations and the set of diagnostic tests, wherein bins of the bin packing operation correspond to the time intervals between or during medical examinations into which one or more diagnostic tests are inserted;

displaying the updated schedule of the medical imaging examinations and the set of diagnostic tests on a display device in operative communication with the electronic processor; and controlling the medical imaging device to perform the set of diagnostic tests in accordance with the updated schedule and the status of the imaging system such that the diagnostic tests are scheduled based on available time and system efficiency taking into account at least one of a last examination that was conducted and a configuration of the medical imaging system.

2. The non-transitory computer readable medium of claim 1, wherein the fitting includes:

imposing a time limit on completion of the set of diagnostic tests wherein all diagnostic tests of the set of diagnostic tests are fitted into the time intervals between or during the medical imaging examinations that precede or end with the imposed time limit.

3. The non-transitory computer readable medium of claim 2, wherein the instructions executable by at least one electronic processor to perform the method of scheduling diagnostic tests includes instructions to:

in a first fitting operation, fit the diagnostic tests of the set of diagnostic tests into the time intervals between or during the medical imaging examinations that precede or end with the imposed time limit; and if the first fitting operation fails, then extend the imposed time limit to define an extended time limit and, in a second fitting operation, fit the diagnostic tests of the set of diagnostic tests into the time intervals between or during the medical imaging examinations that precede or end with the extended time limit.

4. The non-transitory computer readable medium of claim 1, wherein adjustable variables of the bin packing operation include only allocations of the diagnostic tests of the set of diagnostic tests to the bins corresponding to the time intervals.

5. The non-transitory computer readable medium of claim 1, wherein adjustable variables of the bin packing operation include at least one of:

allocations of the diagnostic tests of the set of diagnostic tests to the bins corresponding to the time intervals;

start times of the medical imaging examinations; and a time limit on completion of the set of diagnostic tests wherein all diagnostic tests of the set of diagnostic tests are fitted by the bin packing operation into the time intervals between or during the medical imaging examinations that precede or end with the time limit on completion of the set of diagnostic tests.

6. The non-transitory computer readable medium of claim 1, wherein the receiving includes:

sending a query via an electronic network to an associated hospital scheduling system requesting the schedule of the medical imaging examinations; and receiving the schedule of the medical imaging examinations from the associated hospital scheduling system via the electronic network responsive to the query.

7. The non-transitory computer readable medium of claim 1, wherein the receiving includes at least one of:

receiving the schedule of medical imaging examinations via an electronic network as a spreadsheet; and receiving, via at least one user input device, inputs comprising the schedule of medical imaging examinations.

8. The non-transitory computer readable medium of claim 1, wherein the display device in operative communication with the electronic processor comprises a display device of a workstation that includes the electronic processor or is in operative communication with the electronic processor, the workstation being operable by a remote service engineer.

9. The non-transitory computer readable medium of claim 1, wherein the displaying includes:

sending the updated schedule of the medical imaging examinations and the set of diagnostic tests to an associated hospital scheduling system via an electronic network;

wherein the display device in operative communication with the electronic processor comprises a display device of the associated hospital scheduling system.

10. The non-transitory computer readable medium of claim 1, wherein fitting diagnostic tests into the time intervals between or during medical examinations in the schedule to generate the updated schedule includes:

retrieving a maintenance personnel availability schedule; and in the fitting, setting a time limit for completion of the set of diagnostic tests based on the maintenance personnel availability schedule.

11. The non-transitory computer readable medium of claim 1, wherein the fitting includes:

adjusting a time limit for completion of the set of diagnostic tests including weighting the adjustment of the time limit with a cost factor reflecting a late-service contract penalty.

12. The non-transitory computer readable medium of claim 1, wherein the fitting is repeated iteratively to dynamically update the schedule of the medical imaging examinations and the set of diagnostic tests to account for changes over time in the set of diagnostic tests and/or changes in the schedule of medical imaging examinations.

13. The non-transitory computer readable medium of claim 1, wherein the fitting further includes:

determining a scope of the diagnostic tests; and fitting the diagnostic tests into the time intervals between or during medical examinations based on the determined scope.

14. A non-transitory computer readable medium storing instructions executable by at least one electronic processor to perform a method of scheduling diagnostic tests for a medical imaging device between or during medical imaging examinations, the method comprising:

receiving a schedule of medical imaging examinations, the schedule providing start times of the medical imaging examinations, and time intervals between medical imaging examinations;

fitting diagnostic tests of a set of diagnostic tests into the time intervals between or during the medical imaging examinations in the schedule to generate an updated schedule of the medical imaging examinations and the set of diagnostic tests; and displaying the updated schedule of the medical imaging examinations and the set of diagnostic tests on a display device in operative communication with the electronic processor;

wherein the instructions executable by at least one electronic processor to perform the method of scheduling diagnostic tests includes instructions to:

in a first fitting operation, fit the diagnostic tests of the set of diagnostic tests into the time intervals between or during the medical imaging examinations by adjusting only assignments of the diagnostic tests of the set of diagnostic tests to the time intervals between the medical imaging examinations; and if the first fitting operation fails, then in a second fitting operation, fit the diagnostic tests of the set of diagnostic tests into the time intervals between or during the medical imaging examinations by adjusting both the start times of the medical imaging examinations and the assignments of the diagnostic tests of the set of diagnostic tests to the time intervals between the medical imaging examinations;

wherein the first fitting operation is calculated by $$\sum_{T_j \in f(t)} R_i(T_j) \leq 1, \text{ for every } t \in [0, \omega), \text{ for every } i \in [1, n]$$

where $R_i$ is a given resource, $T_j$ is a diagnostic test, $\omega$ is defined as the time when all tasks have completed; and wherein the method further comprising:

controlling the medical imaging device to perform the set of diagnostic tests in accordance with the updated schedule and the status of the medical imaging device such that the diagnostic tests are scheduled based on available time and system efficiency.

15. The non-transitory computer readable medium of claim 14, wherein the first fitting operation and the second fitting operation are each performed with a time limit on completion of the set of diagnostic tests wherein all diagnostic tests of the set of diagnostic tests are fitted into the time intervals between or during the medical imaging examinations that precede or end with the imposed time limit, and the instructions executable by at least one electronic processor to perform the method of scheduling diagnostic tests includes further instructions to:

if the second fitting fails then in a third fitting operation, fit the diagnostic tests of the set of diagnostic tests into the time intervals between or during the medical imaging examinations by adjusting at least the assignments of the diagnostic tests of the set of diagnostic tests to the time intervals between or during the medical imaging examinations with a longer time limit on the completion of the set of diagnostic tests than the time limit used in the first and second fitting operations.

16. The non-transitory computer readable medium of claim 14, wherein:

the receiving includes sending a query via an electronic network to an associated hospital scheduling system requesting the schedule of the medical imaging examinations, and receiving the schedule of the medical imaging examinations from the associated hospital scheduling system via the electronic network responsive to the query; and the method further includes automatically modifying the schedule of the medical imaging examinations at the associated hospital scheduling system to include the diagnostic tests fitted into the time intervals between or during the medical imaging examinations only if the first fitting operation does not fail.

17. A non-transitory computer readable medium storing instructions executable by at least one electronic processor to perform a method of scheduling diagnostic tests for a medical imaging device between or during medical imaging examinations, the method comprising:

sending a query via an electronic network to an associated hospital scheduling system requesting a schedule of medical imaging examinations;

receiving the schedule of the medical imaging examinations from the associated hospital scheduling system via the electronic network responsive to the query, the schedule providing start times of the medical imaging examinations and time intervals between medical imaging examinations;

fitting diagnostic tests of a set of diagnostic tests into the time intervals between or during the medical imaging examinations in the schedule to generate an updated schedule of the medical imaging examinations and the set of diagnostic tests, wherein the fitting is calculated according to $$F(T_j) = (j-1) \cdot t(T_j), j \cdot t(T_j)), j \in \{1, 2, \ldots, n\}$$

where, $T_j$ is a diagnostic test; and automatically modifying the schedule of the medical imaging examinations at the associated hospital scheduling system to include the diagnostic tests fitted into the time intervals between or during the medical imaging examinations based on the status of the medical imaging device.

18. The non-transitory computer readable medium of claim 17, wherein the method further comprises:

displaying the updated schedule of the medical imaging examinations and the set of diagnostic tests on a display device in operative communication with the electronic processor.

19. The non-transitory computer readable medium of claim 1, wherein the updated schedule is computed according to:

$$f: [0, \omega) \rightarrow 2^{T,}$$

$$f(t) = \{T_i \in T: t \in F(T_i)\}$$

where $\omega$ is defined as the time when all tasks have completed, and $F(T_j) = [\sigma_j, \sigma_j + t(T_j))$, where $\sigma_i$ is the time when the execution of task $T_j$ started.

\* \* \* \* \*